US007241370B2

(12) United States Patent
Taguchi et al.

(10) Patent No.: US 7,241,370 B2
(45) Date of Patent: Jul. 10, 2007

(54) PROTECTIVE COVERS FOR GAS SENSOR, GAS SENSOR AND GAS SENSOR MANUFACTURING METHOD

(75) Inventors: Masataka Taguchi, Gifu (JP); Takahiro Hayashi, Gifu (JP); Yasuhiro Fujita, Gifu (JP); Yoshiaki Matsubara, Nagoya (JP); Hitoshi Iimi, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 644 days.

(21) Appl. No.: 10/446,659

(22) Filed: May 29, 2003

(65) Prior Publication Data

US 2004/0035700 A1    Feb. 26, 2004

(30) Foreign Application Priority Data

Aug. 20, 2002   (JP)   ............... 2002-239354

(51) Int. Cl.
*G01N 27/407* (2006.01)
(52) U.S. Cl. .................... 204/428; 29/592.1
(58) Field of Classification Search ............ 204/424, 204/427, 428, 429; 73/23.31, 23.32; 29/592.1
See application file for complete search history.

(56) References Cited

U.S. PATENT DOCUMENTS

| | | | |
|---|---|---|---|
| 4,717,464 A * | 1/1988 | Oshima et al. ......... | 204/427 |
| 6,068,746 A | 5/2000 | Kojima et al. | |
| 6,258,234 B1 | 7/2001 | Watanabe et al. | |
| 6,279,376 B1 | 8/2001 | Yamada et al. | |
| 6,360,581 B1 | 3/2002 | Murase et al. | |
| 6,792,678 B2 | 9/2004 | Yamada et al. | |
| 2002/0038793 A1 | 4/2002 | Yamada et al. | |
| 2002/0100687 A1 | 8/2002 | Atsumi et al. | |
| 2005/0011063 A1 | 1/2005 | Yamada et al. | |

FOREIGN PATENT DOCUMENTS

| | | |
|---|---|---|
| DE | 195 23 978 A1 | 1/1997 |
| EP | 0 965 838 A1 | 12/1999 |
| EP | 0 974 836 A2 | 1/2000 |
| EP | 1 046 906 A2 * | 10/2000 |

(Continued)

OTHER PUBLICATIONS

European Search Report for EP 03 01 8453 dated Dec. 12, 2003.

*Primary Examiner*—Kaj K. Olsen
(74) *Attorney, Agent, or Firm*—Sughrue Mion, PLLC

(57) ABSTRACT

A gas sensor comprises a cylindrical metallic housing, a sensor element having at a front end thereof a sensing portion and disposed axially in the housing with the sensing portion protruded from a front end of the housing, a sensor terminal fitted to a rear end of the sensor element to produce a signal output from the sensing portion, a first protective cover attached to a front end portion of the housing to cover the sensing portion and a second protective cover attached to a rear end portion of the housing to cover the sensor terminal. The first and second protective covers includes attachment portions attached around the front and rear end portions of the housing, respectively. At least one of the attachment portions of the first and second protective covers has a lower hardness than a remaining portion of the protective cover.

27 Claims, 7 Drawing Sheets

FOREIGN PATENT DOCUMENTS

| | | |
|---|---|---|
| JP | 7-192708 | 7/1995 |
| JP | 10-314870 | 12/1998 |
| JP | 11-352095 | 12/1999 |
| JP | 2000-130434 | 5/2000 |
| JP | 2000-283949 | 10/2000 |
| JP | 2001-147213 | 5/2001 |
| JP | 2002-174622 | 6/2002 |

* cited by examiner

FIG.2
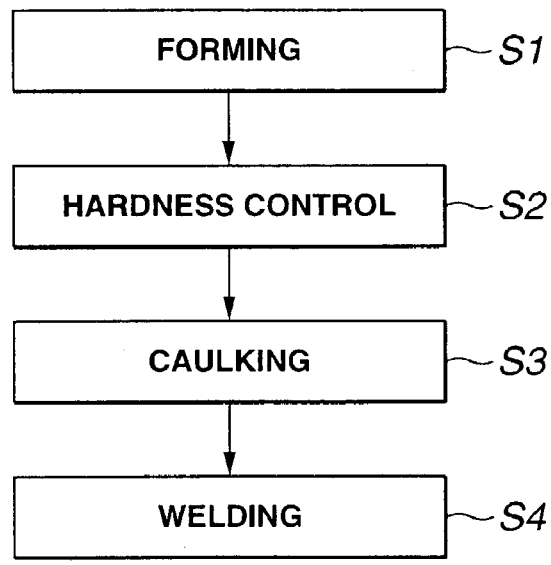
FIG.3A
FIG.3B
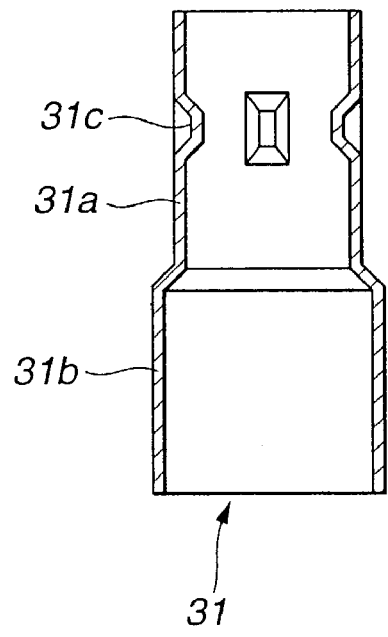
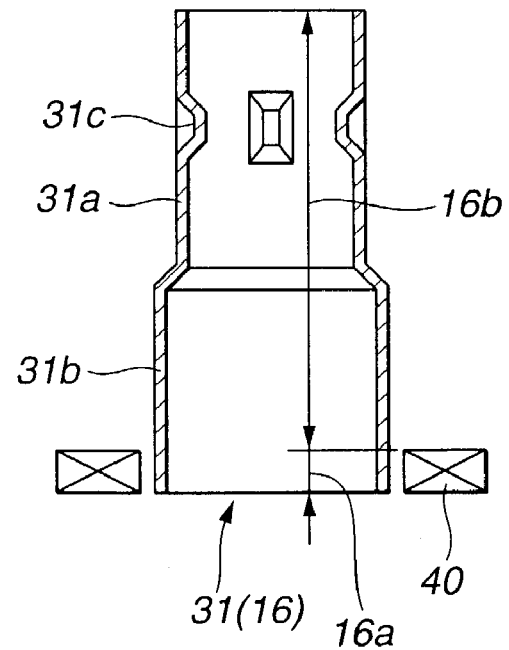

PROTECTIVE COVERS FOR GAS SENSOR, GAS SENSOR AND GAS SENSOR MANUFACTURING METHOD

BACKGROUND OF THE INVENTION

The present invention relates to protective covers for a gas sensor, a gas sensor and a method of manufacturing a gas sensor. Hereinafter, the term "front" refers to a sensing end side with respect to the axial direction of a gas sensor, and the term "rear" refers to a side opposite to the front side.

Japanese Laid-Open Patent Publication No. 11-352095 discloses a conventional type of gas sensor as shown in FIG. 8, which comprises a cylindrical metallic housing 81, a sensor element 82, a heater 83, metallic protective covers 84 and 85, a ground terminal 91, an output terminal 92, a ground lead 93, an output lead 94, a pair of heater terminals 95 (only one shown) and heater leads (not shown). The housing 81 has a metallic shell 81a and an inner tube 81b fixed to each other, although it can alternatively be formed into one piece. The sensor element 82 is disposed axially in the housing 81 with a sensing portion thereof protruded from a front end of the housing 81, and the heater 83 is inserted in the sensor element 82. The ground and output terminals 91 and 92 are fitted to a rear end of the sensor element 82 to make electrical connection between the sensor element 82 and the ground and output leads 93 and 94, whereas the heater terminals 95 are fitted to a rear end of the heater 95 to make electrical connection between the heater 83 and the heater leads. The protective cover 84 is attached to a front end portion of the housing 81 to cover the sensing portion of the sensor element 82. The protective cover 85 is attached to a rear end portion of the housing 81 to cover the ground and output terminals 91 and 92 and the heater terminals 95 with the ground and output leads 93 and 94 and the heater leads projected rearwardly from the protective cover 85.

SUMMARY OF THE INVENTION

In the above conventional type gas sensor, there is a difficulty in attaching the protective covers 84 and 85 to the housing 81.

It has been common practice to attach a protective cover to a sensor housing by forming an engaging part on the protective cover, engaging the housing with the engaging part of the protective cover, and then, welding the engaging part of the cover protective to the housing. However, stringent dimensional control is required for proper engagement between the housing and the engaging part of the protective cover. The processing and inspection of the housing and the protective cover are time-and labor-consuming, thereby resulting in a high manufacturing cost of the gas sensor. In the case of the protective cover being formed by drawing austenitic stainless steel, the protective cover is easily expansible due to elasticity. It is specifically burdensome and thus costly to perform stringent dimensional control in the processing and inspection of such an easily expansible protective cover.

Against this backdrop, another cover attachment method is proposed in Japanese Laid-Open Patent Publication No. 11-352095, in which portions 84a and 85a of the protective covers 84 and 85 are caulked to front and rear end portions of the housing 81 and then welded at weld sections W1 and W2 to the housing 81. This makes it possible to simplify the processing and inspection of the housing 81 and the protective covers 84 and 85 without the need for stringent dimensional control and thereby possible to reduce the manufacturing cost of the gas sensor.

In the above proposed method, however, the portions 84a and 85a of the protective covers 84 and 85 have inside diameters considerably larger than the outside diameters of the front and rear end portions of the housing 81 before being caulked so that the portions 84a and 85a of the protective covers 84 and 85 can be easily disposed around the housing 81. It is not easy to caulk such large-diameter portions 84a and 85a of the protective covers 84 and 85 to the housing 81 assuredly, as the protective covers 84 and 85 have relatively large thicknesses so as to protect the sensing portion and the terminals 91, 92 and 95 from external shocks. Nevertheless, there cannot be clearance left between the housing 81 and the portions 84a and 85a of the protective covers 84 and 85 in order to weld the portions 84a and 85a of the protective covers 84 and 85 to the housing 81 securely. Accordingly, the portions 84a and 85a of the protective covers 84 and 85 have to be caulked through the application of high pressure, which causes deteriorations in the durability of a caulking tool etc. The manufacturing cost of the gas sensor cannot be then reduced sufficiently.

It is conceivable to form the protective covers 84 and 85 from a relatively soft material so that the portions 84a and 85a of the protective covers 84 and 85 can be caulked without the application of high pressure. This makes it possible to reduce the manufacturing cost of the gas sensor to a sufficient degree. However, the protective covers 84 and 85 become too weak to act as protections against the external shocks. The gas sensor cannot attain sufficient durability for use in e.g. a vehicle.

If the protective cover 84 has a double-wall structure, there arises an additional problem that the gas sensor delays in responding to a sudden change in measurement gas.

It is therefore an object of the present invention to provide protective covers for a gas sensor, which can be attached to a sensor housing easily and assuredly to cover a sensor element and sensor terminals without causing the above-mentioned cost and durability problems, as well as a gas sensor having such a protective cover(s) and a method of manufacturing the gas sensor.

It is also an object of the present invention to provide a gas sensor with a double-wall protective cover, which shows a higher responsivity.

According to a first aspect of the invention, there is provided a protective cover for a gas sensor having a cylindrical metallic housing and a sensor element axially disposed in the housing with a sensing portion thereof protruded from a front end of the housing, the protective cover including an attachment portion to be attached around a front end portion of the housing in such a manner as to cover the sensing portion with the protective cover, the attachment portion having a lower hardness than a remaining portion of the protective cover.

According to a second aspect of the invention, there is provided a protective cover for a gas sensor having a cylindrical metallic housing, a sensor element axially disposed in the housing and having at a front end thereof a sensing portion and a sensor terminal fitted to a rear end of the sensor element to produce a signal output from the sensing portion, the protective cover including an attachment portion to be attached around a rear end portion of the housing in such a manner as to cover the sensor terminal with the protective cover, the attachment portion having a lower hardness than a remaining portion of the protective cover.

According to a third aspect of the invention, there is provided a gas sensor, comprising: a cylindrical metallic housing; a sensor element having at a front end thereof a sensing portion and disposed axially in the housing with the sensing portion protruded from a front end of the housing; a sensor terminal fitted to a rear end of the sensor element to produce a signal output from the sensing portion; a first protective cover attached to a front end portion of the housing to cover the sensing portion, the first protective cover including an attachment portion attached around the front end portion of the housing; and a second protective cover attached to a rear end portion of the housing to cover the sensor terminal, wherein the attachment portion has a lower hardness than a remaining portion of the first protective cover.

According to a fourth aspect of the invention, there is provided a gas sensor, comprising: a cylindrical metallic housing; a sensor element having at a front end thereof a sensing portion and disposed axially in the housing with the sensing portion protruded from a front end of the housing; a sensor terminal fitted to a rear end of the sensor element to produce a signal output from the sensing portion; a first protective cover attached to a front end portion of the housing to cover the sensing portion; and a second protective cover attached to a rear end portion of the housing to cover the sensor terminal, the second protective cover including an attachment portion attached around the rear end portion of the housing, wherein the attachment portion has a lower hardness than a remaining portion of the second protective cover.

According to a fifth aspect of the invention, there is provided a gas sensor, comprising: a cylindrical metallic housing; a sensor element having at a front end thereof a sensing portion and disposed axially in the housing with the sensing portion protruded from a front end of the housing; a sensor terminal fitted to a rear end of the sensor element to produce a signal output from the sensing portion; a first protective cover attached to a front end portion of the housing to cover the sensing portion; and a second protective cover attached to a rear end portion of the housing to cover the sensor terminal, wherein the first protective cover has: an outer cover member including an attachment portion attached around the rear end portion of the housing and an outer circumferential wall, the outer circumferential wall having outer gas inlet holes formed therein to feed a measurement gas into the outer cover member; and an inner cover member fixed in the outer cover member and including an inner circumferential wall held in parallel with the outer circumferential wall and at a rear end thereof a wall edge bent to the outer circumferential wall, the wall edge having inner gas inlet holes formed therein to feed the measurement gas from the outer cover member into the inner cover member.

According to a sixth aspect of the invention, there is provided a method of manufacturing a gas sensor, comprising: disposing a sensor element in a cylindrical metallic housing, the sensor element having at a front end thereof a sensing portion protruded from a front end of the housing; forming a protective cover with an attachment portion; making a hardness of the attachment portion lower than that of a remaining portion of the protective cover; and attaching the attachment portion of the protective cover around a front end portion of the housing in such a manner as to cover the sensing portion with the protective cover.

According to a seventh aspect of the invention, there is provided a method of manufacturing a gas sensor, comprising: disposing a sensor element in a cylindrical metallic shell, the sensor element having at a front end thereof a sensing portion; fitting a sensor terminal to a rear end of the sensor element for signal output from the sensing portion; forming a protective cover with an attachment portion; making a hardness of the attachment portion lower in hardness than that of a remaining portion of the protective cover; and attaching the attachment portion of the protective cover around a rear end portion of the housing in such a manner as to cover the sensor terminal with the protective cover.

BRIEF DESCRIPTION OF THE DRAWINGS

FIG. 2 is a process chart for manufacturing the oxygen sensor.

FIG. 3A is a sectional view of a terminal cover of the oxygen sensor, after the process of forming.

FIG. 3B is a sectional view of the terminal cover of FIG. 3A, during the process of hardness control.

DESCRIPTION OF THE EMBODIMENTS

The present invention will be described below with reference to the drawings. Although the present invention can be applied to various kinds of sensors including a gas concentration sensor that detects the concentration of a specific component of a measurement gas (such as an oxygen sensor, a HC sensor or a NOx sensor) and a gas temperature sensor that detects the temperature of a measurement gas, the following embodiment specifically refers to an oxygen sensor.

Figure 1:
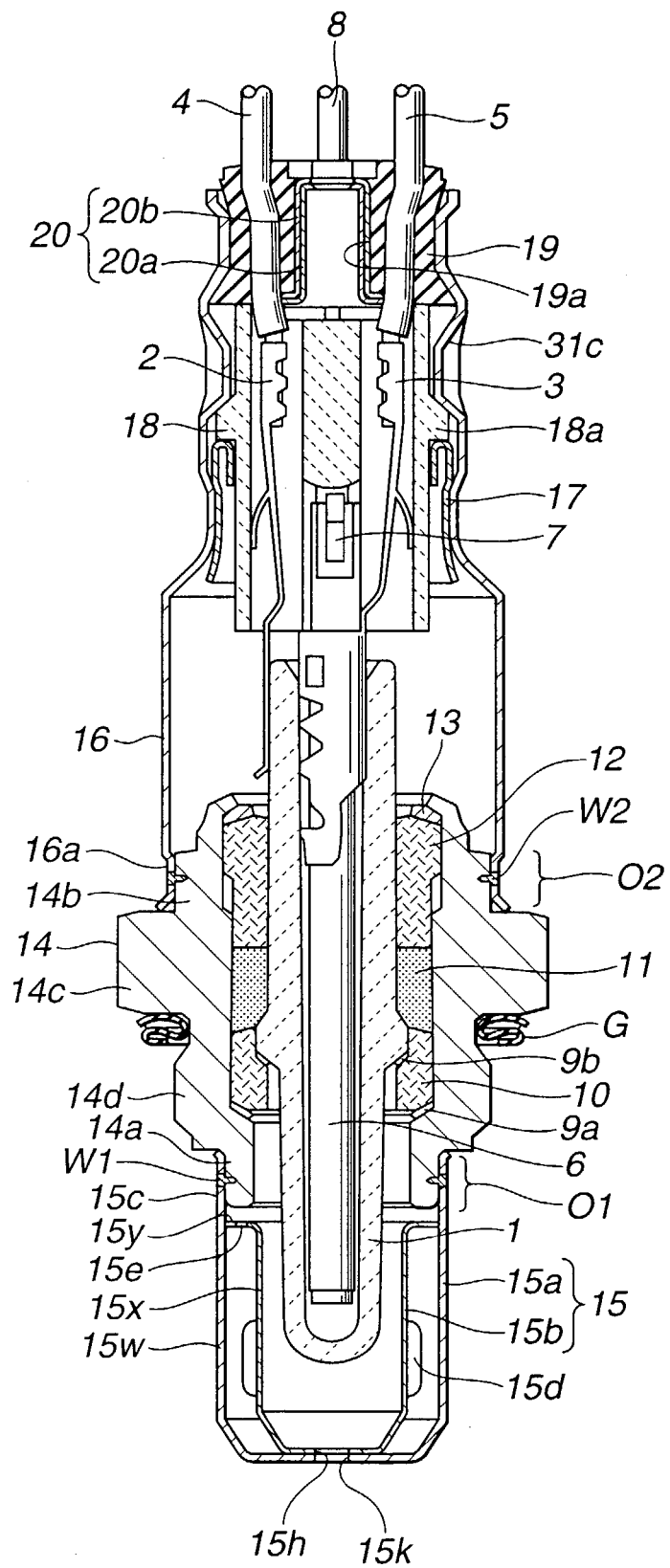
FIG. 1 is a sectional view of an oxygen sensor according to one embodiment of the present invention.

As shown in FIG. 1, an oxygen sensor according to one embodiment of the present invention comprises a sensor element 1, a ground terminal 2, an output terminal 3, a ground lead 4, an output lead 5, a heater 6, a pair of heater terminals 7 (only one shown), heater leads 8 (only one shown), a cylindrical metallic shell 14 (as a sensor housing) and metallic protective covers 15 and 16.

The sensor element 1 has at a front end thereof a sensing portion to detect the concentration of oxygen in a measurement gas. The sensor element 1 includes a cylindrical element body having its front end closed, an inner electrode layer formed on an inner surface of the body, and an outer electrode layer formed on an outer surface of the body. The element body is made of a solid electrolyte e.g. zirconium oxide ($ZrO_2$) stabilized with yttrium oxide ($Y_2O_3$) or calcium oxide (CaO), whereas the inner and outer electrode layers are made of e.g. platinum (Pt).

The ground and output terminals 2 and 3 are fitted to a rear end of the sensor element 1. The ground terminal 2 makes electrical connection between the outer electrode layer of the sensor element 1 and the ground lead 4 to establish a ground for the sensor element 1, and the output terminal 3 makes electrical connection between the inner electrode layer of the sensor element 1 and the output lead to retrieve an output signal from the sensing portion of the sensor element 1.

The heater 6 is inserted in the body of the sensor element 1, and the heater terminals 7 are fitted to a rear end of the heater 6. The heater leads 8 are connected to the respective heater terminals 7 for energization of the heater 6.

The sensor element 1 is axially disposed in the metallic shell 14 with the sensing portion protruded from a front end of the metallic shell 14. Metallic packings 9a and 9b, a ceramic holder 10, a sealant 11 made of e.g. talc, a ceramic sleeve 12 and a metallic ring 13 are interposed between the sensor element 1 and the metallic shell 14. A rear end portion of the metallic shell 14 is caulked radially inwardly to the sensor element 1 via the ceramic sleeve 12, so that the sensor element 1 is held in the metallic shell 14 while being kept insulated from the metallic shell 14.

The metallic shell 14 includes front and rear cylindrical boss end portions 14a and 14b, a flange portion 14c, and a male-thread portion 14d formed between the boss end portion 14a and the flange portion 14c. A gasket G is fitted around the metallic shell 14 at a position between the flange portion 14c and the male-thread portion 14d.

Figure 4:
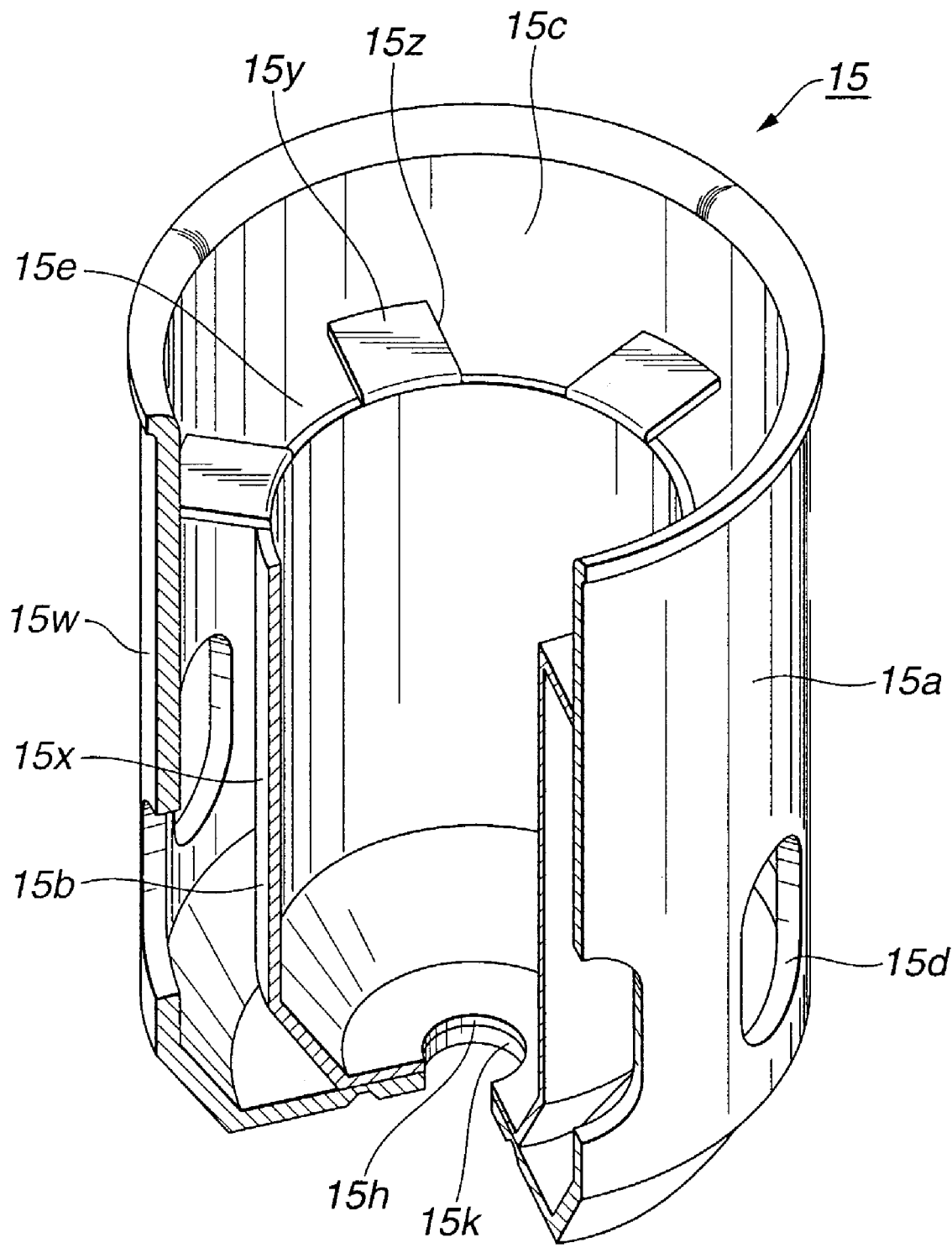
FIG. 4 is a partially cutaway view of a sensor-element cover of the oxygen sensor.
Figure 5:
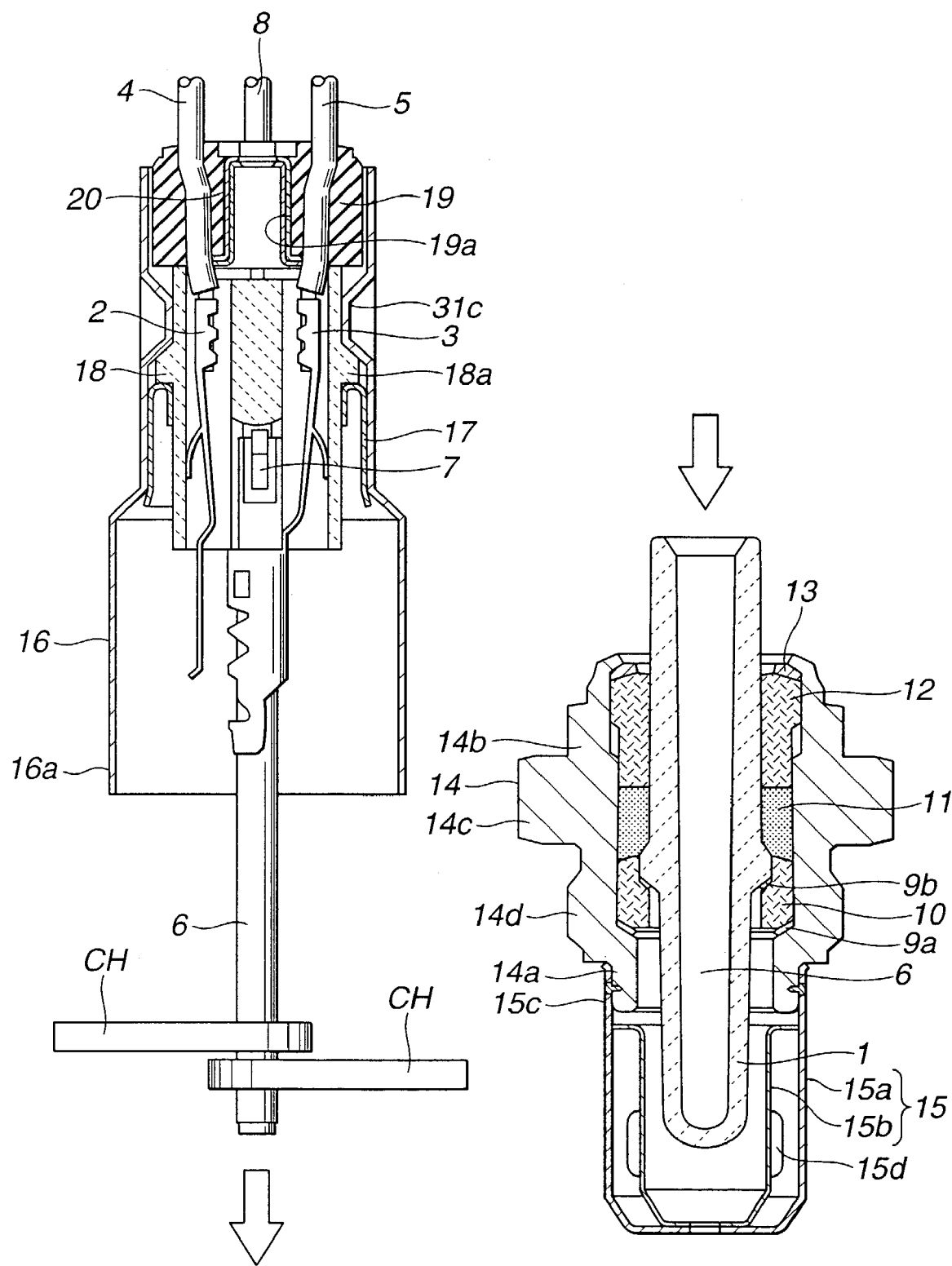
FIG. 5 is a sectional view showing how the oxygen sensor comes assembled.

The protective cover 15 is attached to the boss end portion 14a of the metallic shell 14 to cover the sensing portion of the sensor element 1. Preferably, the protective cover 15 has a double-wall structure with an outer cover member 15a and an inner cover member 15b fixed in the outer cover member 15a as shown in FIG. 4.

The outer cover member 15a has a circumferential wall 15w and a cylindrical attachment portion 15c formed integral with the circumferential wall 15w at a rear end of the outer cover member 15a. The attachment portion 15c is disposed around the boss end portion 14a of the metallic shell 14 to form an overlap O1 between the attachment portion 15c and the boss end portion 14a, and is attached to the boss end portion 14a by caulking and welding at the overlap O1.

The inner cover member 15b has a circumferential wall 15x held in parallel to the circumferential wall 15w with a predetermined space left therebetween, and at a rear end thereof a wall edge 15y brought into contact with an inner surface of the circumferential wall 15w.

In the present embodiment, the attachment portion 15c has a lower hardness than that of a remaining portion of the cover 15 (including the circumferential walls 15x and 15y and the wall edge 15y), so that the attachment portion 15c can be easily and assuredly caulked to the boss end portion 14a of the metallic shell 14 without clearance left between the attachment portion 15c and the boss end portion 14a. It is preferable that the attachment portion 15c has a Vickers hardness of 100 to 200 and the remaining portion of the cover 15 has a Vickers hardness of 300 to 400. If the Vickers hardness of the attachment portion 15c is lower than 100, the attachment portion 15c cannot secure sufficient strength after the caulking and welding. If the Vickers hardness of the attachment portion 15c is higher than 200, it is difficult to caulk the attachment portion 15c to the boss end portion 14a assuredly while making the protective cover 15 with a relatively large thickness. The remaining portion of the cover 15 becomes too weak to act as a protection against external shocks and to attain sufficient durability if the Vickers hardness of the remaining portion of the cover 15 is lower than 300. If the Vickers hardness of the remaining portion of the cover 15 is higher than 400, the remaining portion becomes susceptible to cracks due to its brittleness and difficult to form. Herein, the Vickers hardness is defined as an average of measurement values obtained in Vickers hardness test with a load of 300 g applied at established axial intervals (e.g. every 0.5 mm in the present embodiment) to an axial section through the protective cover 15 at half of its radial thickness.

Each of the attachment portion 15c and the remaining portion of the cover 15 preferably has a thickness of 0.4 mm or larger so as to attain sufficient shock resistance. The attachment portion 15c and the remaining portion of the cover 15 are desirably 1.0 mm or smaller in thickness in consideration of formability. In a case where the protective cover 15 has the above double-wall structure, it is preferable that the outer cover member 15a has a thickness of 0.4 mm to 1.0 mm and the inner cover member 15b has a thickness of less than 0.4 mm. The inner cover member 15b does not necessarily require so high durability as the outer cover member 15a. Accordingly, the inner cover member 15b can be made thinner than the outer cover member 15a for downsizing of the oxygen sensor. In the present embodiment, the outer and inner cover members 15a and 15b are made 0.5 mm and 0.3 mm in thickness, respectively.

The attachment portion 15c and the remaining portion of the cover 15 are preferably made of austenitic stainless steel such as SUS304L or SUS310.

In a case where the protective cover 15 has a total length of 20 to 50 mm, the attachment portion 15c preferably has a length of 5 to 7 mm. If the length of the attachment portion 15c is less than 5 mm, it is difficult to caulk and weld the attachment portion 15c to the boss end portion 14a. If the length of the attachment portion 15c is more than 7 mm, the remaining portion of the cover 15 becomes too short to act as a protection against external shocks and to attain sufficient durability. In the present embodiment, the protective cover 15 and its attachment portion 15a are made 20 mm and 5 mm in length, respectively. Further, the inner cover member 15b has a length shorter than that of the outer cover member 15a so that the protective cover 15 is attached to the metallic shell 14 only at the attachment portion 15c of the outer cover member 15b. It is easier to caulk and weld the attachment portion 15c directly to the metallic shell 14 than to caulk and weld the attachment portion 15c via the inner cover member 15b to the metallic housing 14.

Gas inlet holes 15d and 15e are formed in the circumferential wall 15w of the outer cover member 15a and the wall edge 15y of the inner cover member 15b, respectively, so as to feed the measurement gas to the sensing portion of the sensor element 1. In order for the wall edge 15y to be easily formed with the gas inlet holes 15e, cuts 15z are made in the wall edge 15y, and then, the wall edge 15y is bent to the circumferential wall 15w in such a manner as to bring the wall edge 15y into contact with the inner surface of the circumferential wall 15w. With this, the gas inlet holes 15e are easily defined by the cuts 15z of the wall edge 15y and the circumferential wall 15w so as to face toward a gas passage between the circumferential walls 15x and 15y.

Gas outlet holes 15h and 15k are formed in bottoms of the inner and outer cover members 15b and 15a, respectively, to discharge the measurement gas out of the protective cover 15. In the present embodiment, the outer and inner cover members 15a and 15b are joined together by e.g. spot welding at positions around the gas outlet holes 15k and 15h in order to prevent the gas from flowing directly from the gas inlet hole 15d to the gas outlet hole 15k.

In the above double-wall structure of the protective cover 15, the measurement gas flows into the outer cover member 15a via the gas inlet holes 15d, flows rearwardly through the gas passage between the circumferential walls 15x and 15w, flows into the inner cover member 15b via the gas inlet holes 15*e*, flows through a gas passage between the wall edge 15*y* and the boss end portion 14*a*, flows frontwardly within the inner cover member 15*b* to be supplied to the sensing portion, and then, flows out of the protective cover 15 through the gas outlet holes 15*h* and 15*k*. As the gas inlet holes 15*e* face toward the gas passage between the circumferential walls 15*x* and 15*y*, the measurement gas flows into the inner cover member 15*b* without a large flow resistance. Further, the measurement gas flows within the inner cover member 15*b* in such a manner as to force a gas holdup in the cover member 15*b* toward the gas outlet holes 15*h* and 15*k*. Gas replacement can be therefore performed smoothly within the protective cover 15 by such a zigzag flow. Even if there is a sudden change in oxygen concentration, the oxygen sensor becomes able to provide a quick response to such a sudden change. Namely, the oxygen sensor of the present embodiment can attain higher responsivity than a conventional oxygen sensor with a double-wall sensor cover.

Herein, there is a possibility that the flow of gas to the sensing portion of the sensor element 1 may be prevented due to a water drop accumulated in the gas passage between the wall edge 15*y* and the boss end portion 14*a*. In order to avoid such a possibility, it is preferable to make the thickness of a front edge of the boss end portion 14*a* smaller than a length of the wall edge 15*y* (i.e. a distance between the circumferential walls 15*x* and 15*w* of the cover members 15*b* and 15*a*), or to form the cuts 15*z* over the wall edge 15*y* and the circumferential wall 15*x*.

The protective cover 16 is attached to the boss end portion 14*b* of the metallic shell 14 to cover the ground and output terminals 2 and 3 and the heater terminals 7 with the ground and output leads 4 and 5 and the heater leads 8 projected rearwardly from the protective cover 16.

The protective cover 16 includes at a front end thereof a cylindrical attachment portion 16*a*. The attachment portion 16*a* is disposed around the boss end portion 14*b* to form an overlap O2 between the attachment portion 16*a* and the boss end portion 14*b*, and is attached to the boss end portion 14*b* by caulking and welding at the overlap O2.

In the present embodiment, the attachment portion 16*a* has a lower hardness than that of a remaining portion 16*b* of the cover 16, so that the attachment portion 16*a* can be easily and assuredly caulked to the boss end portion 14*b* of the metallic shell 14 without clearance left between the attachment portion 16*a* and the boss end portion 14*b*. It is preferable that the attachment portion 16*a* has a Vickers hardness of 100 to 200 and the remaining portion 16*b* has a Vickers hardness of 300 to 400. If the Vickers hardness of the attachment portion 16*a* is lower than 100, the attachment portion 16*a* cannot attain sufficient strength after the caulking and welding. If the Vickers hardness of the attachment portion 16*a* is higher than 200, it is difficult to caulk the attachment portion 16*a* to the boss end portion 14*b* assuredly while making the protective cover 16 with a relatively large thickness. The remaining portion 16*b* becomes too weak to act as a protection against external shocks and to attain sufficient durability if the Vickers hardness of the remaining portion 16*b* is lower than 300. If the Vickers hardness of the remaining portion 16*b* is higher than 400, the remaining portion 16*b* becomes susceptible to cracks due to its brittleness and difficult to form. Herein, the Vickers hardness is defined in the same way as above i.e. as an average of measurement values obtained in Vickers hardness test with a load of 300 g applied at established axial intervals (e.g. every 0.5 mm) to an axial section through the protective cover 16 at half of its radial thickness.

Each of the attachment portion 16*a* and the remaining portion 16*b* of the cover 16 preferably has a thickness of 0.4 mm or larger so as to attain sufficient shock resistance. The thickness of each of the attachment portion 16*a* and the remaining portion 16*b* is desirably 1.0 mm or smaller in consideration of formability. In the present embodiment, both of the attachment portion 16*a* and the remaining portion 16*b* are made 0.5 mm in thickness.

The attachment portion 16*a* and the remaining portion 16*b* of the cover 16 are preferably made of austenitic stainless steel such as SUS304L or SUS310.

In a case where the protective cover 16 has a total length of 20 to 50 mm, the attachment portion 16*a* is preferably made 5 to 7 mm in length. If the length of the attachment portion 16*a* is less than 5 mm, it is difficult to caulk and weld the attachment portion 16*a* to the boss end portion 14*b*. If the length of the attachment portion 16*a* is more than 7 mm, the remaining portion 16*b* of the cover 16 becomes too short to act as a protection against external shocks and to attain sufficient durability. In the present invention, the protective cover 16 and its attachment portion 16*a* are made 47 mm and 6 mm in length, respectively.

A ceramic separator 18 with a flange portion 18*a* is fixed in the protective cover 16*a* via a leaf spring 17 so that the separator 18 surrounds the connection between the ground terminal 2 and the lead 4, the connection between the output terminal 3 and the lead 5 as well as the respective connections between the heater terminals 7 and the leads 8.

A rubber grommet 19 is fix in a rear end of the protective cover 16 with the sensor leads 4 and 5 and the heater leads 8 passing therethrough. The grommet 19 has a through hole 19*a* at a center thereof, and a filter unit 20 is disposed in the hole 19*a*. The filter unit 20 has a cylindrical metallic support 20*a* and a filter 20*b* attached to cover a rear end face and a circumferential portion of the support 20*a*. The filter 20*b* is made of e.g. polytetrafluoroethylene (PTFE), and removes moisture from the air so that dehydrated air is supplied to the inside of the protective cover 16.

The above-structured oxygen sensor can be manufactured by the following procedure according to one embodiment of the present invention.

Firstly, all the components of the oxygen sensor (including the sensor element 1, the ground terminal 2, the output terminal 3, the ground lead 4, the output lead 5, the heater 6, the heater terminals 7, the heater leads 8, the packings 9*a* and 9*b*, the holder 10, the sealant 11, the sleeve 12, the ring 13, the metallic shell 4, the protective covers 15 and 16, the spring 17, the separator 18, the grommet 19 and the filter unit 20) are prepared. In particular, the protective covers 15 and 16 can be prepared in the following forming and hardness control process steps (as in steps S1 and S2 of FIG. 2).

To prepare the protective cover 16, a plate or pipe of austenitic stainless steel is subjected to drawing to form a tubular article 31 having a small-diameter part 31*a* and a large-diameter part 31*b* formed integral with the small-diameter part 31*a* as shown in FIG. 3A. Four radially-inward protrusions 31*c* are formed by drawing on the small-diameter part 31*a* so as to be engageable with the flange portion 18*a* of the separator 18. Then, only an open-end side of the large-diameter part 31*b* (which corresponds to the attachment portion 16*a* of the protective cover 16) is annealed by placing a high-frequency coil 40 around the open-end side of the large-diameter part 31*b* as shown in FIG. 3B, supplying the coil 40 with a high-frequency current to subject the open-end side of the part 31*b* to high-frequency induction heating at about 700° C., and cooling the annealed open-end side of the part 31b in the air. Alternatively, the annealing can be done by using an electron beam. With the annealing, the attachment portion 16a is made lower in hardness than the remaining portion 16b. It is preferable to control the Vickers hardness of the attachment portion 16a to within the range of 100 to 200 and to control the Vickers hardness of the remaining portion 16b to within the range of 100 to 200 as described above. Further, the attachment portion 16a has an inside diameter considerably larger than an outside diameter of the boss end portion 14b of the metallic shell 14 so that the attachment portion 16a can be easily arranged around the boss end portion 14b.

The protective cover 15 can be prepared in the same manner. With the annealing, the attachment portion 15c is also made lower in hardness than the remaining portion of the cover 15 at relatively low cost. As described above, it is preferable to control the Vickers hardness of the attachment portion 15c to within the range of 100 to 200 and to control the Vickers hardness of the remaining portion of the cover 15 to within the range of 300 to 400. Further, the attachment portion 15c has an inside diameter larger than an outside diameter of the boss end portion 14a of the metallic shell 14 so that the attachment portion 15c can be easily arranged around the boss end portion 14a.

Next, the prepared components are combined into first and second subassemblies.

The first subassembly is provided by: passing the leads 4, 5 and 8 through the grommet 19, and then, through the separator 18; connecting the ground and output terminals 2 and 3 to the leads 4 and 5, respectively; and connecting the heater 6 to the leads 8 via the respective heater terminals 7; putting the leaf spring 17 on a front end portion of the separator 18; inserting the separator 18 in the protective cover 16 until the flange portion 18a of the separator 18 abuts on the protrusions 31c; and inserting the grommet 19 in the rear end of the cover 16.

The second subassembly is provided by: inserting the packing 9a, the holder 19 and the packing 9b in the metallic shell 14 in order of mention; placing the sensor element 1 in the metallic shell 14 so as to be surrounded by the packing 9a, the holder 10 and the packing 9b; arranging the sealant 11, the sleeve 12 and the ring 13 between the sensor element 1 and the metallic shell 14; caulking the rear end portion of the metallic shell 14 to the sensor element 1 via the sleeve 12; putting the protective cover 15 on the metallic shell 14 so that the attachment portion 15c circumferentially surrounds the boss end portion 14a to form the overlap O1; caulking the attachment portion 15c to the boss end portion 14a (as in step S3 of FIG. 2); and welding the attachment portion 15c and the boss end portion 14a together (as in step S4 of FIG. 2). In the present embodiment, the attachment portion 15c is circumferentially caulked to the boss end portion 14a (i.e. the overlap O1 between the attachment portion 15c is caulked radially inwardly) in order to perform the subsequent welding step without difficulty and thereby fix the protective cover 15 to the metallic shell 14 securely. The caulking can be done by using a caulking tool equipped with a roller or six or more punches. Preferably, a caulking tool with eight or more punches is used so that the attachment portion 15c is assuredly caulked to the boss end portions 14 throughout its circumference by surrounding the attachment portion 15c with the punches. The attachment portion 15c is also circumferentially welded to the boss end portion 14a (i.e. a circumferential weld section W1 is formed in the overlap O1 between the attachment portion 15c and the boss end portion 14a) in order to fix the protective cover 15 to the metallic housing 14 securely, although the attachment portion 15c can alternatively be joined to the boss portion 14a by spot welding. For ease of welding, it is preferable to weld the attachment portion 15c circumferentially by using a laser beam.

Figure 6:
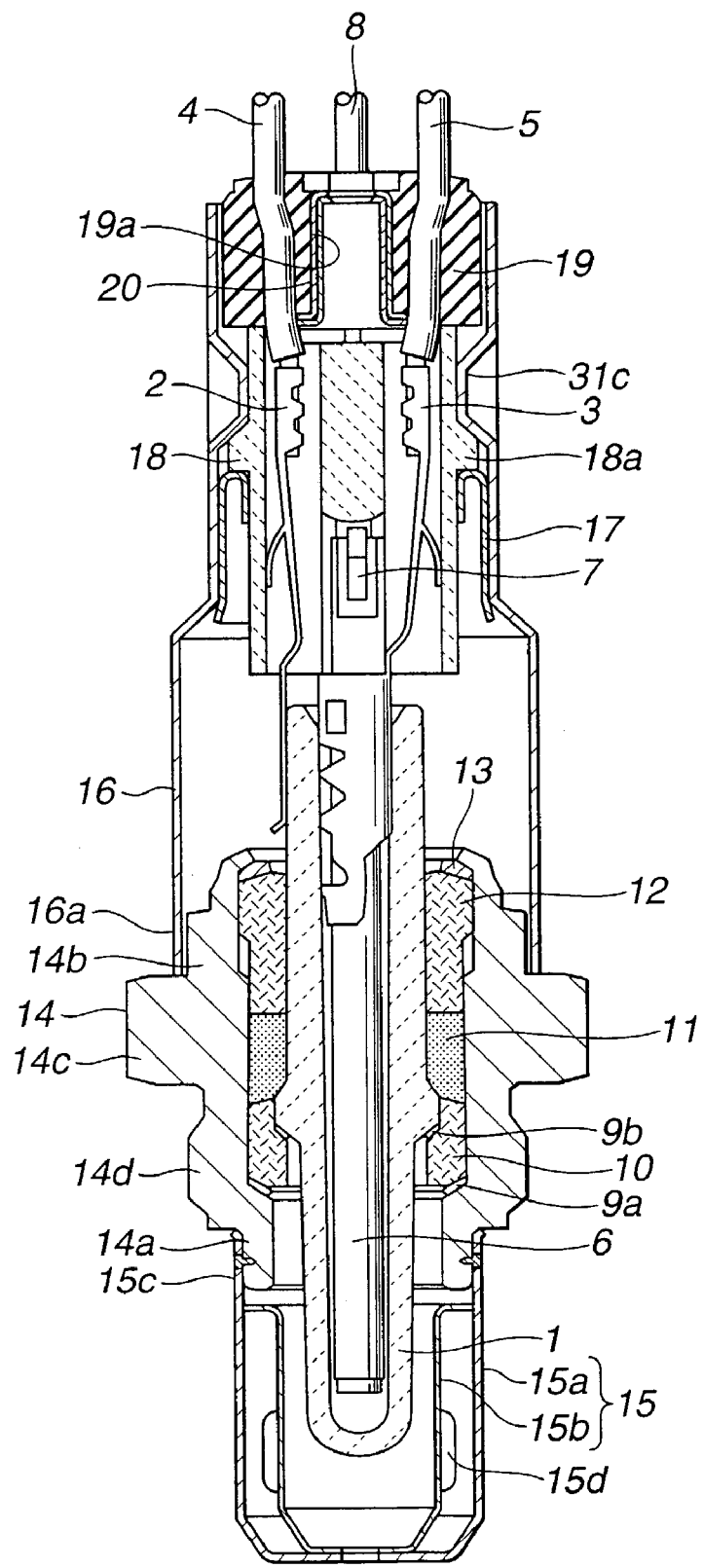
FIG. 6 is a sectional view of the oxygen sensor in a condition where the terminal cover is not yet caulked.

While the first subassembly is supported with chucks CH, the heater 6 of the second subassembly is inserted into the body of the sensor element 1 of the first subassembly until the protective cover 16 of the first subassembly abuts on the flange portion 14c of the metallic shell 14 of the second subassembly. While inserting the heater 6 into the body of the sensor element 1, the electrical connection is made between the ground terminal 2 and the outer electrode layer of the sensor element 1 and between the output terminal 3 and the inner electrode layer of the sensor element 1. At this time, the oxygen sensor comes assembled as shown in FIG. 6, with a radial space left between the attachment portion 16a of the protective cover 16 and the boss end portion 14b of the metallic shell 14.

Then, the attachment portion 16a is caulked and welded to the boss end portion 14b (as in steps S3 and S4 of FIG. 2). In order to perform the subsequent welding step without difficulty and thereby fix the protective cover 15 to the metallic shell 14 securely, the attachment portion 16a is circumferentially caulked to the boss end portion 14b (i.e. the overlap O2 between the attachment portion 16a and the boss end portion 14b is caulked radially inwardly). The caulking can be done by using a caulking tool equipped with a roller or six or more punches. Preferably, a caulking tool with eight or more punches is used so that the attachment portion 16a is assuredly caulked to the boss end portion 14b throughout its circumference by surrounding the attachment portion 16a with the punches. The attachment portion 16a is also circumferentially welded to the boss end portion 14b (i.e. a circumferential weld section W2 is formed in the overlap O2 between the attachment portion 16a and the boss end portion 14b) in order to fix the protective cover 16 to the metallic housing 14 securely, although the attachment portion 16a can alternatively be joined to the boss end portion 14b by spot welding. For ease of welding, it is preferable to weld the attachment portion 16a *circumferentially by using a laser beam*.

Finally, the protective cover 16 is caulked radially inwardly at a position axially corresponding to the leaf spring 17 so as to hold the separator 18 with the flange portion 18a sandwiched between the protrusions 31c of the cover 16 and the leaf spring 17, and is caulked at a position axially corresponding to the grommet 18. The oxygen sensor is then completed as shown in FIG. 1.

For use of the oxygen sensor, the oxygen sensor is mounted in e.g. an exhaust pipe of a vehicle. When the measurement gas is supplied to the sensing portion of the sensor element 1 via the gas inlet holes 15d and 15e, there arises an electromotive force between the inner and outer electrode layers of the sensor element 1 in accordance with the concentration of oxygen in the measurement gas. The electromotive force is outputted as a signal from the inner electrode layer through the output terminal 3 and the output lead 5, whereas the outer electrode layer is grounded through the ground terminal 2 and the ground lead 4. During the measurement of oxygen concentration, the protective cover 15 protects the sensing portion from water or oil drops, and the protective cover 16 protects the sensing portion and the terminals 2, 3 and 6 from flying gravel etc. Further, the filter unit 20 feeds dehydrated air into the protective cover 16 by means of the filter 20b so as to set a standard for the output signal. The heater 6 is energized through the heater terminals 7 and the leads 8 for quick actuation of the sensing portion.

As described above, the attachment portions 15c and 16a of the protective covers 15 and 16 are made lower in hardness. The attachment portions 15c and 16a can be therefore caulked to the boss end portions 14a and 14b of the metallic housing 14 easily and assuredly without clearance therebetween, even when the protective covers 15 and 16 have relatively large thicknesses so as to protect the sensor element 1 and the terminals 2, 3 and 7 from external shocks and when the attachment portions 15c and 16a have relatively large inside diameters than outside diameters of the boss end portions 14a and 14b so as to be easily arranged around the boss end portions 14a and 14b. Even in the case of the protective covers 15 and 16 being formed by drawing austenitic stainless steel, there is no need to perform stringent dimensional control for engagement between the attachment portion 15c and the boss end portion 14a and between the attachment portion 16a and the boss end portion 14b. Also, there is no need to apply high pressure to caulk the attachment portions 15c and 16a, thereby avoiding deteriorations in the durability of the caulking tool etc. The above assuredly caulked attachment portions 15c and 16a can be welded to metallic shell 4 easily and assuredly at sufficient weld strength. The protective covers 15 and 16 properly work to protect the sensor element 1 and the terminals 2, 3 and 7 from external shocks because the protective covers 15 and 16 have relatively large thickness and the remaining portions of the covers 15 and 16 are higher in hardness. It becomes possible according to the present embodiment of the invention to simplify the manufacturing process of the oxygen sensor for reduction in manufacturing cost while securing sufficient durability for the oxygen sensor under use in the vehicle.

The present invention will be specifically illustrated in more detail by way of the following examples. However, it should be noted that the following example is only illustrative and not intended to limit the present invention thereto.

EXAMPLE

A protective cover (corresponding to the cover 16 in the above embodiment) was formed from SUS304L with the following dimensions as shown in FIG. 3A. Only an attachment portion of the cover was annealed using a high-frequency coil as shown in FIG. 3B.

| [Dimensions] | Length of the cover: | 47 mm |
| --- | --- | --- |
| | Length of the attachment portion: | 6 mm |
| | Thickness of the cover: | 0.5 mm |

Figure 7:
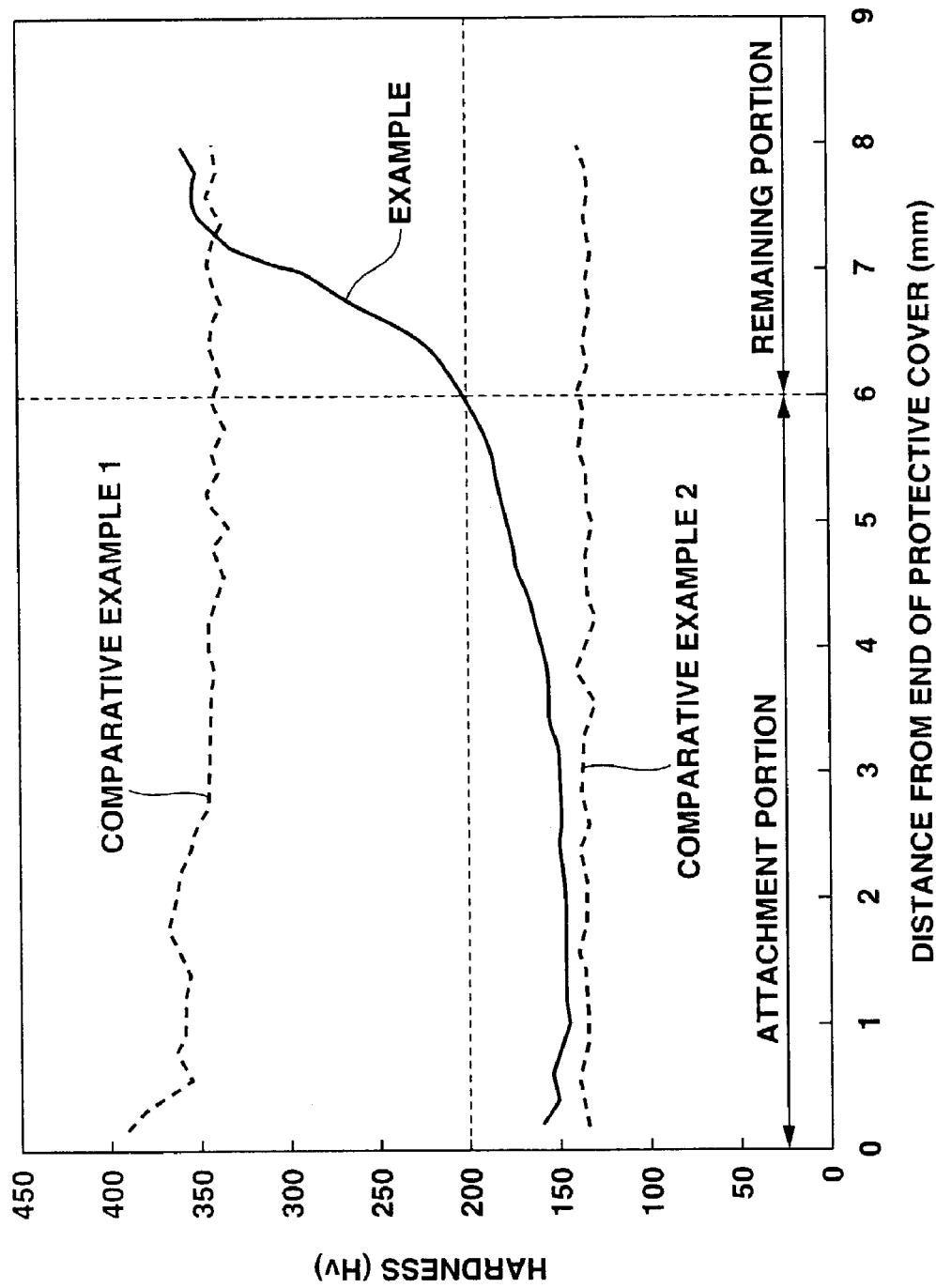
FIG. 7 is a graph showing the relationship between a hardness and a location on the terminal cover.
Figure 8:
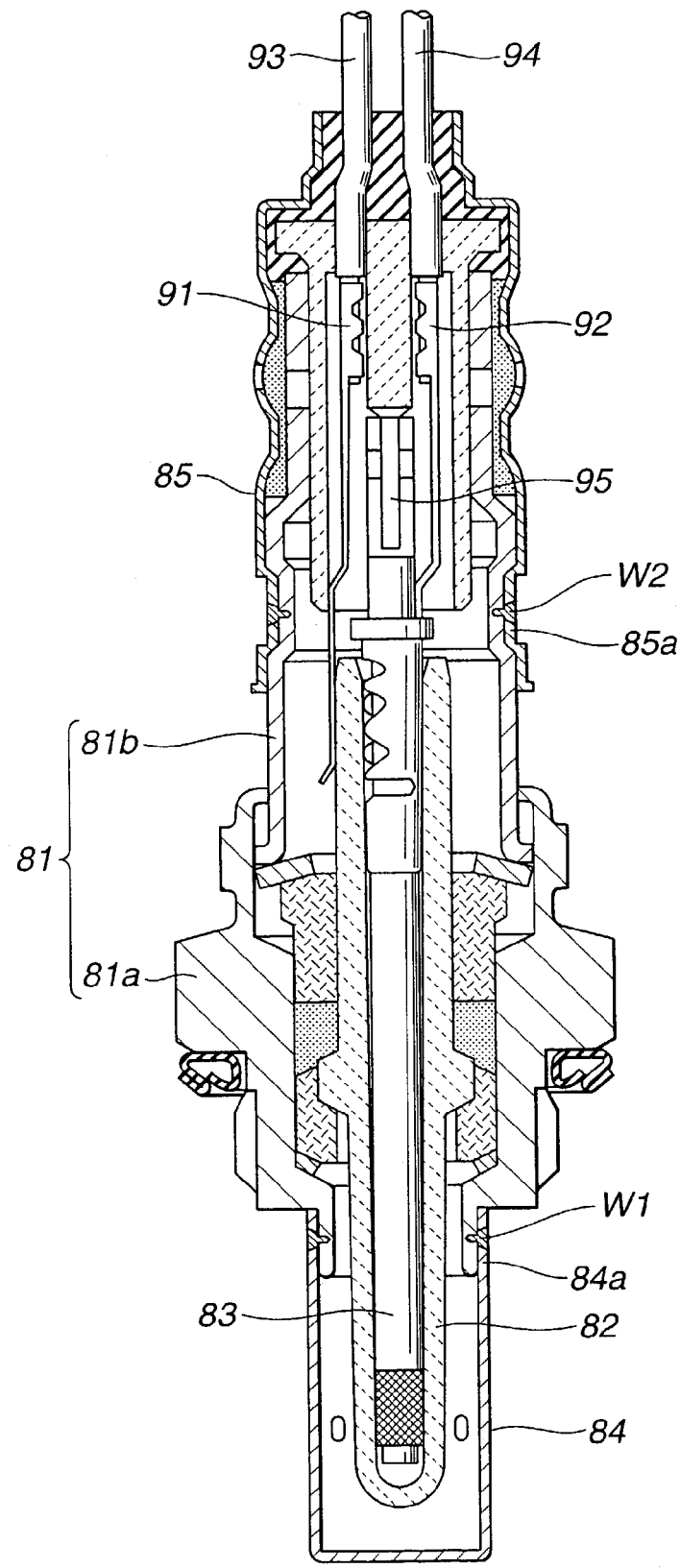
FIG. 8 is a sectional view of a conventional type gas sensor.

The prepared protective cover showed hardness characteristics as shown in FIG. 7. Namely, the attachment portion had a Vickers hardness of 100 to 200 mm, and the remaining portion of the cover had a Vickers hardness of 300 to 400 (on average).

An oxygen sensor was assembled using the prepared protective cover in compliance with the above-described embodiment. The caulking was done by using a caulking tool with eight punches, and the welding was done by laser welding. The attachment portion of the cover was caulked easily and assuredly without causing deteriorations in the durability of the punches etc. Further, the protective cover was able to satisfactorily act as a protection. It is thus possible to reduce the manufacturing cost of the oxygen sensor while securing sufficient durability for the sensor by the use of the protective cover of EXAMPLE.

Comparative Example 1

The same procedure as in EXAMPLE was repeated, except the entire cover was not given annealing. As shown in FIG. 7, the prepared protective cover had a Vickers hardness of 300 to 400 throughout its length. In the assembling of the oxygen sensor, the attachment portion of the cover was caulked by the application of increased pressure to cause deteriorations in the durability of the punches etc. It is thus concluded that the manufacturing cost of the oxygen sensor cannot be reduced sufficiently by the use of the protective cover of COMPARATIVE EXAMPLE 1.

Comparative Example 2

The same procedure as in EXAMPLE was repeated, except that the entire cover was given annealing. The prepared protective cover had a Vickers hardness of 200 or lower throughout its length, as shown in FIG. 7. In the assembling of the oxygen sensor, the attachment portion of the protective cover was caulked without causing deteriorations in the durability of the punches etc. However, the protective cover was too weak to act as a protection against external shocks. It is thus concluded that the oxygen sensor does attain sufficient durability by the use of the protective cover of COMPARATIVE EXAMPLE 2 although the manufacturing cost of the sensor can be reduced.

The entire contents of Japanese Patent Application No. 2002-239354 (filed on Aug. 20, 2002) are herein incorporated by reference.

Although the present invention has been described with reference to a specific embodiment of the invention, the invention is not limited to the above-described embodiment. Various modification and variation of the embodiment described above will occur to those skilled in the art in light of the above teaching. For example, either one of the attachment portions 15c and 16a of the protective covers 15 and 16 may have a lower hardness than that of the remaining portion. Further, the sensor housing may have a cylindrical metallic shell and an inner tube fixed to each other by e.g. caulking. The scope of the invention is defined with reference to the following claims.

What is claimed is:

1. A gas sensor, comprising:
   a cylindrical metallic housing;
   a sensor element having at a front end thereof a sensing portion and disposed axially in the housing with the sensing portion protruded from a front end of the housing;
   a sensor terminal fitted to a rear end of the sensor element to produce a signal output from the sensing portion;
   a first protective cover attached to a front end portion of the housing to cover the sensing portion, the first protective cover including an attachment portion attached around the front end portion of the housing; and
   a second protective cover attached to a rear end portion of the housing to cover the sensor terminal,
   wherein the attachment portion has a lower hardness than a remaining portion of the first protective cover.

2. The gas sensor according to claim 1, wherein the attachment portion of the first protective cover is attached around the front end portion of the housing by caulking and welding.

3. The gas sensor according to claim 1, wherein the attachment portion of the first protective cover is circumferentially welded to the front end portion of the housing.

4. The gas sensor according to claim 1, wherein the first protective cover comprises an outer cover member and an inner cover member fixed in the outer cover member to cover the sensing portion, and the attachment portion is formed on the outer cover member.

5. The gas sensor according to claim 4, wherein the outer cover member includes an outer circumferential wall; the outer circumferential wall has outer gas inlet holes formed therein to feed a measurement gas into the outer cover member; the inner cover member includes an inner circumferential wall held in parallel with the outer circumferential wall and at a rear end thereof a wall edge bent to the outer circumferential wall; and the wall edge of the inner cover member has inner gas inlet holes formed therein to feed the measurement gas from the outer cover member into the inner cover member.

6. The gas sensor according to claim 5, wherein the wall edge of the inner cover member has cuts formed therein to define the inner gas inlet holes.

7. The gas sensor according to claim 4, wherein the outer cover member has a thickness of 0.4 mm or greater, and the inner cover member has a smaller thickness than that of the outer cover member.

8. A gas sensor, comprising:
a cylindrical metallic housing;
a sensor element having at a front end thereof a sensing portion and disposed axially in the housing with the sensing portion protruded from a front end of the housing;
a sensor terminal fitted to a rear end of the sensor element to produce a signal output from the sensing portion;
a first protective cover attached to a front end portion of the housing to cover the sensing portion; and
a second protective cover attached to a rear end portion of the housing to cover the sensor terminal, the second protective cover including an attachment portion attached around the rear end portion of the housing,
wherein the attachment portion has a lower hardness than a remaining portion of the second protective cover.

9. The gas sensor according to claim 8, wherein the attachment portion of the second protective cover is attached around the rear end portion of the housing by caulking and welding.

10. The gas sensor according to claim 8, wherein the attachment portion of the second protective cover is circumferentially welded to the rear end portion of the housing.

11. The gas sensor according to claim 8, wherein the second protective cover is integrally formed of said attachment portion and said remaining portion.

12. The gas sensor according to claim 8, wherein the attachment portion is formed in the front end of the second protective cover.

13. A gas sensor, comprising:
a cylindrical metallic housing;
a sensor element having at a front end thereof a sensing portion and disposed axially in the housing with the sensing portion protruded from a front end of the housing;
a sensor terminal fitted to a rear end of the sensor element to produce a signal output from the sensing portion;
a first protective cover attached to a front end portion of the housing to cover the sensing portion; and
a second protective cover attached to a rear end portion of the housing to cover the sensor terminal,
wherein the first protective cover has:
an outer cover member including an attachment portion attached around the front end portion of the housing and an outer circumferential wall, the outer circumferential wall having outer gas inlet holes formed therein to feed a measurement gas into the outer cover member; and
an inner cover member fixed in the outer cover member and including an inner circumferential wall held in parallel with the outer circumferential wall and at a rear end thereof a wall edge bent to the outer circumferential wall, the wall edge having inner gas inlet holes formed therein to feed the measurement gas from the outer cover member into the inner cover members,
wherein the attachment portion has a lower hardness than a remaining portion of the first protective cover.

14. The gas sensor according to claim 13, wherein the wall edge of the inner cover member has cuts formed therein, and the inner gas inlet holes are defined by the cuts of the wall edge and the outer circumferential wall.

15. The gas sensor according to claim 13, wherein the outer cover member has a larger thickness than that of the inner cover member.

16. A method of manufacturing a gas sensor, said gas sensor comprising:
a cylindrical metallic housing;
a sensor element having at a front end thereof a sensing portion and disposed axially in the housing with the sensing portion protruded from a front end of the housing;
a sensor terminal fitted to a rear end of the sensor element to produce a signal output from the sensing portion;
a first protective cover attached to a front end portion of the housing to cover the sensing portion, the first protective cover including an attachment portion attached around the front end portion of the housing; and
a second protective cover attached to a rear end portion of the housing to cover the sensor terminal,
wherein the attachment portion has a lower hardness than a remaining portion of the first protective cover,
said method comprising:
disposing a sensor element in a cylindrical metallic housing, the sensor element having at a front end thereof a sensing portion protruded from a front end of the housing;
forming a protective cover with an attachment portion;
making a hardness of the attachment portion lower than that of a remaining portion of the protective cover; and
attaching the attachment portion of the protective cover around a front end portion of the housing in such a manner as to cover the sensing portion with the protective cover.

17. The method according to claim 16, wherein the attaching comprises:
arranging the attachment portion of the first protective cover around the front end portion of the housing;
caulking the attachment portion of the first protective cover to the front end portion of the housing; and
circumferentially welding the attachment portion of the protective cover to the front end portion of the housing.

18. The method according to claim 17, wherein the welding is laser welding.

19. The method according to claim 16, wherein the first protective cover is formed by drawing austenitic stainless steel.

20. The method according to claim 16, wherein the hardness of the attachment portion is made lower by annealing.

21. The method according to claim 20, wherein the annealing is performed by high-frequency induction heating.

22. A method of manufacturing a gas sensor, said gas sensor comprising:
- a cylindrical metallic housing;
- a sensor element having at a front end thereof a sensing portion and disposed axially in the housing with the sensing portion protruded from a front end of the housing;
- a sensor terminal fitted to a rear end of the sensor element to produce a signal output from the sensing portion;
- a first protective cover attached to a front end portion of the housing to cover the sensing portion; and
- a second protective cover attached to a rear end portion of the housing to cover the sensor terminal, the second protective cover including an attachment portion attached around the rear end portion of the housing,
- wherein the attachment portion has a lower hardness than a remaining portion of the second protective cover, said method comprising:
- disposing a sensor element in a cylindrical metallic shell, the sensor element having at a front end thereof a sensing portion;
- fitting a sensor terminal to a rear end of the sensor element for signal output from the sensing portion;
- forming said second protective cover with an attachment portion;
- making a hardness of the attachment portion lower in hardness than that of a remaining portion of the second protective cover; and
- attaching the attachment portion of the second protective cover around a rear end portion of the housing in such a manner as to cover the sensor terminal with the second protective cover.

23. The method according to claim 22, wherein the attaching comprises:
- arranging the attachment portion of said second protective cover around the rear end portion of the housing;
- caulking the attachment portion of the second protective cover to the rear end portion of the housing; and
- circumferentially welding the attachment portion of the second protective cover to the rear end portion of the housing.

24. The method according to claim 23, wherein the welding is laser welding.

25. The method according to claim 22, wherein the second protective cover is formed by drawing austenitic stainless steel.

26. The method according to claim 22, wherein the hardness of the attachment portion is made lower by annealing.

27. The method according to claim 26, wherein the annealing is performed by high-frequency induction heating.

* * * * *